United States Patent
Rezai et al.

(10) Patent No.: US 7,831,308 B2
(45) Date of Patent: Nov. 9, 2010

(54) NEURAL STIMULATION DELIVERY DEVICE WITH INDEPENDENTLY MOVEABLE DELIVERY STRUCTURES

(75) Inventors: Ali Rezai, Bratenhal, OH (US); Ashwini Sharan, Mt. Laurel, NJ (US)

(73) Assignee: The Cleveland Clinic Foundation, Cleveland, OH (US)

( * ) Notice: Subject to any disclaimer, the term of this patent is extended or adjusted under 35 U.S.C. 154(b) by 948 days.

(21) Appl. No.: 10/502,348

(22) PCT Filed: Jan. 31, 2003

(86) PCT No.: PCT/US03/02845

§ 371 (c)(1),
(2), (4) Date: Nov. 16, 2004

(87) PCT Pub. No.: WO03/066153

PCT Pub. Date: Aug. 14, 2003

(65) Prior Publication Data

US 2005/0075681 A1   Apr. 7, 2005

Related U.S. Application Data

(60) Provisional application No. 60/353,705, filed on Feb. 1, 2002.

(51) Int. Cl.
*A61N 1/372* (2006.01)
(52) U.S. Cl. ...................................... 607/48
(58) Field of Classification Search ............... 600/373, 600/378, 393, 544; 607/45, 116, 117, 118
See application file for complete search history.

(56) References Cited

U.S. PATENT DOCUMENTS

| | | | |
|---|---|---|---|
| 4,522,212 A | 6/1985 | Gelinas et al. | |
| 5,034,004 A | 7/1991 | Crankshaw | |
| 5,237,996 A | 8/1993 | Waldman et al. | |
| 5,257,634 A * | 11/1993 | Kroll ......................... | 607/122 |
| 5,366,490 A | 11/1994 | Edwards et al. | |
| 5,496,369 A | 3/1996 | Howard, III | |
| 5,606,975 A | 3/1997 | Liang et al. | |

(Continued)

OTHER PUBLICATIONS

Webster's Ninth New Collefiate Dictionary, (Springfield Massachusetts: Merriam-Webster Inc., Publishers, 1990), 285, 737.*

(Continued)

*Primary Examiner*—Carl H Layno
*Assistant Examiner*—Frances P Oropeza
(74) *Attorney, Agent, or Firm*—Kenyon & Kenyon LLP

(57) ABSTRACT

The present invention relates to a neural stimulation delivery device to deliver electrical and/or chemical stimulation to target sites in the central and peripheral nervous system. The device generally includes a tubular body defining a plurality of ports along the longitudinal axis thereof, a plurality of delivery structures insertable in the body, and a control mechanism in communication with the plurality of delivery structures to independently move each of the plurality of delivery structures through a respective one of the plurality of ports with respect to each other of the plurality of delivery structures. The ability of each delivery structure to be independently moveable through a respective port allows each delivery structure to be selectively advanced or retracted independent of the movement of another delivery structure.

29 Claims, 16 Drawing Sheets

U.S. PATENT DOCUMENTS

| | | | |
|---|---|---|---|
| 5,697,975 A | 12/1997 | Howard, III et al. | |
| 5,711,316 A | 1/1998 | Elsberry et al. | |
| 5,713,922 A | 2/1998 | King | |
| 5,836,874 A * | 11/1998 | Swanson et al. | 600/374 |
| 5,843,093 A | 12/1998 | Howard, III | |
| 6,050,992 A | 4/2000 | Nichols | |
| 6,129,685 A | 10/2000 | Howard, III | |
| 6,192,279 B1 | 2/2001 | Barreras, Sr. et al. | |
| 6,208,881 B1 * | 3/2001 | Champeau | 600/374 |
| 6,301,492 B1 * | 10/2001 | Zonenshayn | 600/378 |
| 6,337,998 B1 | 1/2002 | Behl et al. | |
| 6,343,226 B1 | 1/2002 | Sunde et al. | |
| 6,353,762 B1 * | 3/2002 | Baudino et al. | 607/45 |
| 6,485,482 B1 * | 11/2002 | Belef | 604/528 |
| 6,663,622 B1 * | 12/2003 | Foley et al. | 606/34 |
| 2002/0018317 A1 | 2/2002 | Sato | |
| 2002/0062143 A1 | 5/2002 | Baudino et al. | |
| 2002/0095202 A1 | 7/2002 | Schmidt | |
| 2002/0147484 A1 | 10/2002 | Dahl et al. | |

OTHER PUBLICATIONS

Search Report from PCT/US03/02845.

* cited by examiner

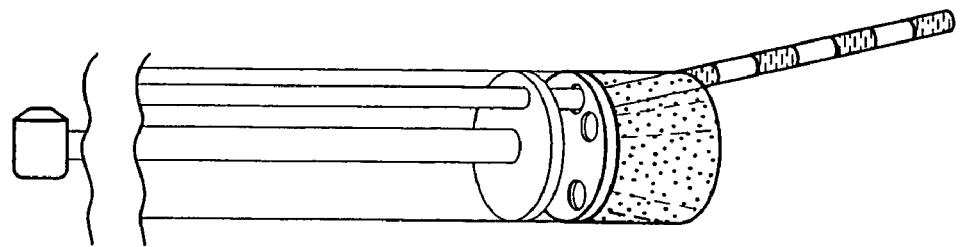
FIG. 26E
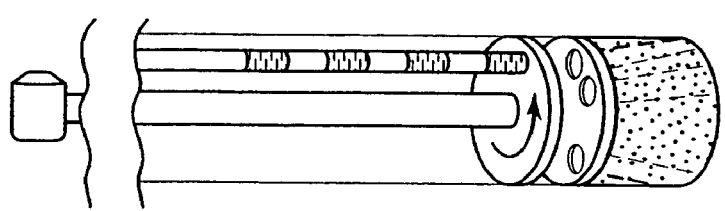
FIG. 26D
FIG. 26C
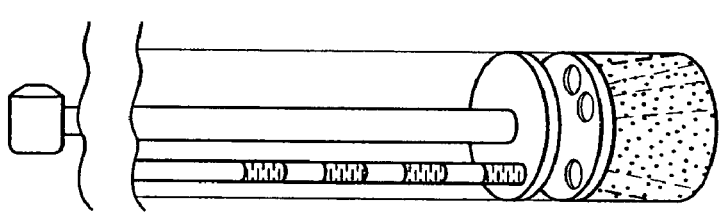
FIG. 26B
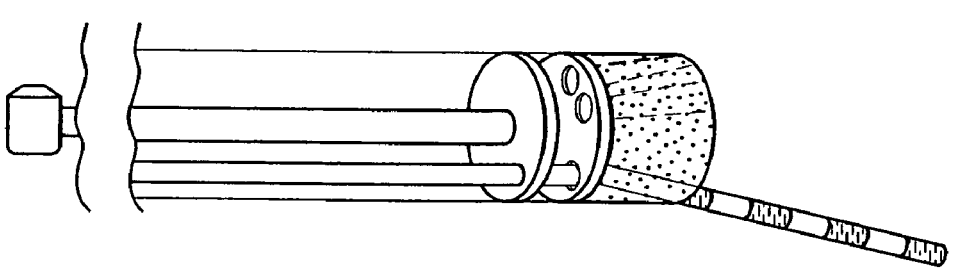
FIG. 26A
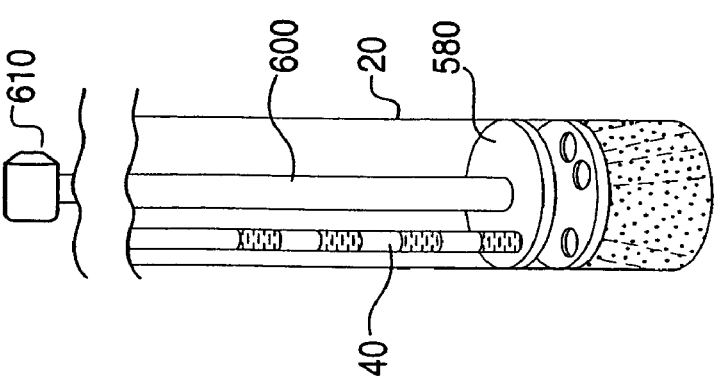

NEURAL STIMULATION DELIVERY DEVICE WITH INDEPENDENTLY MOVEABLE DELIVERY STRUCTURES

CROSS-REFERENCE TO RELATED APPLICATIONS

This is a 371 application of PCT/US03/02845 filed 31 Jan. 2003, the content of which is incorporated herein by reference.

This application also claims priority to Provisional U.S. Application No. 60/353,705 filed Feb. 1, 2002, which is incorporated herein by reference.

FIELD OF THE INVENTION

The present invention relates to a device for electrically and/or chemically stimulating neural tissue.

BACKGROUND OF THE INVENTION

Electrical stimulation of neural tissue is becoming an increasingly preferred form of therapy for various neurological conditions and disorders. Such therapy provides distinct advantages over surgical lesioning techniques, which are still being used to affect disorders and conditions such as Parkinson's disease, essential tremors and dystonia. In particular, unlike surgical lesioning techniques, electrical stimulation is a reversible and adjustable procedure that provides continuous benefits as the patient's disease progresses and the patient's symptoms evolve.

Electrical stimulation of neural tissue to affect a particular neurological condition is typically performed by implanting near a specific site of neural tissue a device including an electrical lead having one or more electrodes. The lead is coupled to a signal generator that delivers electrical energy through the electrodes to the neural tissue stimulating an increase, decrease, or block of neuronal activity to directly or indirectly affect the neurological condition. In order to perform this procedure effectively, a practitioner must position the electrical stimulation device in such a way to modulate the desired volume of neural tissue and to minimize stimulating unwanted adjacent neural tissue, which could create undesirable side effects. Such precise targeting to focus stimulation towards a specific location sub-serving the desired function to be modulated requires enormous time and effort. Furthermore, often times the stimulation must be adjusted or redirected after the initial surgery as a result of sub-optimal placement, lead migration, disease progression, inefficacious treatment, undesirable side effects, neural plasticity, or histological changes of tissue surrounding the stimulation device.

With present multi-contact electrode devices, it is hard to overcome these problems since it is difficult to redirect stimulation after the initial surgery even though limited readjustments can be made by selecting a different contact combination, pulse rate, pulse width or voltage. Stimulation devices have been described to purportedly address the deficiencies of these multi-contact electrode devices, but none provide an optimal alternative. For example, U.S. Patent Publication 2002/018317 describes a directional brain stimulation lead assembly including a lead body and an insulating member defining one or more windows that selectively expose portions of electrodes carried by the lead body to produce a directional stimulation current field. Because of the configuration of the electrodes, however, the distance of electrical stimulation in the radial direction is limited. Therefore, the lead assembly may not be able to effect therapy to neural tissue sites located outside the assembly's radius of stimulation. U.S. Pat. No. 6,353,762 describes a device including electrical leads inserted into a cannula and projecting outward at the distal end of the cannula. Because the leads only project from the distal end of the cannula, the area over which stimulation can be provided is limited. For example, if it is desired to stimulate a new neural tissue site located superior or inferior to the original stimulation site, the device's position must be readjusted to raise or lower the device so that the leads are positioned in a location adjacent to this new neural site. Such readjustment may require a second surgery if the decision to reposition the device is made after the initial surgery, thereby increasing the risk of bleeding and damage to surrounding neural tissue and increasing the cost of the overall therapy.

Therefore, there is an unmet need for a versatile neural stimulation delivery device that allows for varying directions, distances, and degrees of stimulation to sufficiently reduce the time, cost, and risk of electrical stimulation of neural tissue.

SUMMARY OF INVENTION

The present invention discloses a stimulation delivery device to stimulate neural tissue generally including a plurality of independently moveable delivery structures. The delivery structures may provide electrical stimulation in which case the delivery structures are leads or leads having delivery elements that are electrodes disposed thereon. The leads are, in turn, coupled to a signal generator. Alternatively or in addition, the delivery structures may provide chemical stimulation in which case the delivery structures are catheters defining delivery elements that are drug ports. The catheters are, in turn, coupled to a drug pump. The delivery structures may non-destructively stimulate any type of neural tissue including any areas of the central nervous system and peripheral nervous system such as the brain, spinal cord, and peripheral nerves. Although the device of the present invention is particularly adapted for deep brain stimulation, the device may be implanted epidurally, subdurally, intracranially, or cortically.

In particular, one embodiment of the present invention provides a stimulation delivery device for stimulating neural tissue including a body having a proximal end and a distal end and defining a plurality of ports along a longitudinal axis thereof between the proximal end and the distal end of the body. The device also includes a plurality of delivery structures insertable within the body, each of the plurality of delivery structures independently moveable through a respective one of the plurality of ports. In a preferred embodiment, the device also includes at least one delivery element disposed on the body.

Another embodiment of the present invention provides a stimulation delivery device for stimulating neural tissue comprising a body having a proximal end and a distal end, the body defining an annular arrangement of a plurality of ports between the proximal end and the distal end of the body about a plane transverse to the longitudinal axis of the body. The device further includes a plurality of delivery structures insertable in the body, each of the plurality of delivery structures independently moveable through a respective one of the plurality of ports.

Another embodiment of the present invention provides a stimulation delivery device for stimulating neural tissue comprising a body having a proximal end and a distal end, the body defining a semi-annular arrangement of a plurality of ports between the proximal end and the distal end of the body about a plane transverse to the longitudinal axis of the body.

The device further includes a plurality of delivery structures insertable in the body, each of the plurality of delivery structures independently moveable through a respective one of the plurality of ports.

Another embodiment of the present invention provides a stimulation delivery device for stimulating neural tissue comprising a body having a proximal end and a distal end and defining a plurality of ports at the distal end thereof. The device further includes a plurality of delivery structures insertable within the body, each of the delivery structures independently moveable through a respective one of the plurality of delivery structures.

Another embodiment of the present invention provides a stimulation delivery system for stimulating neural tissue comprising a stimulation delivery device and a control mechanism. The stimulation delivery device comprises a body having a proximal end and a distal end and defining a plurality of ports along the longitudinal axis thereof between the proximal end and the distal end of the body. The stimulation delivery device further comprises a plurality of delivery structures insertable within the body. The control mechanism is in communication with the plurality of delivery structures to independently move each of the plurality of delivery structures through a respective one of the plurality of ports.

BRIEF DESCRIPTION OF DRAWINGS

The present invention will become more fully understood from the detailed description given hereinbelow and the accompanying drawings which are given by way of illustration only, and thus are not limitative of the present invention, and wherein:

FIGS. 26A-26E depict alternative deployments of the device of FIG. 25.

DETAILED DESCRIPTION OF INVENTION

The present invention relates to a neural stimulator delivery device with independently moveable delivery structures. As illustrated diagrammatically in FIG. 1, device 10 may be implanted in brain B of patient P to modulate a neural tissue target site of brain B to affect a neurological condition. As illustrated schematically in FIG. 2, in a preferred system, device 10 is implanted within a target site of brain B and coupled to a therapy delivery device 500, such as a pulse generator or drug pump to produce electrical or chemical stimulation pulses that are sent to device 10 to electrically or chemically stimulate the target site. A connector 510, which is an insulated conductor in the case of electrical stimulation, couples therapy delivery device 500 to device 10. Therapy delivery device 500 is, in turn, implanted in the abdomen or any other part of a patient P's body.

Figure 3:
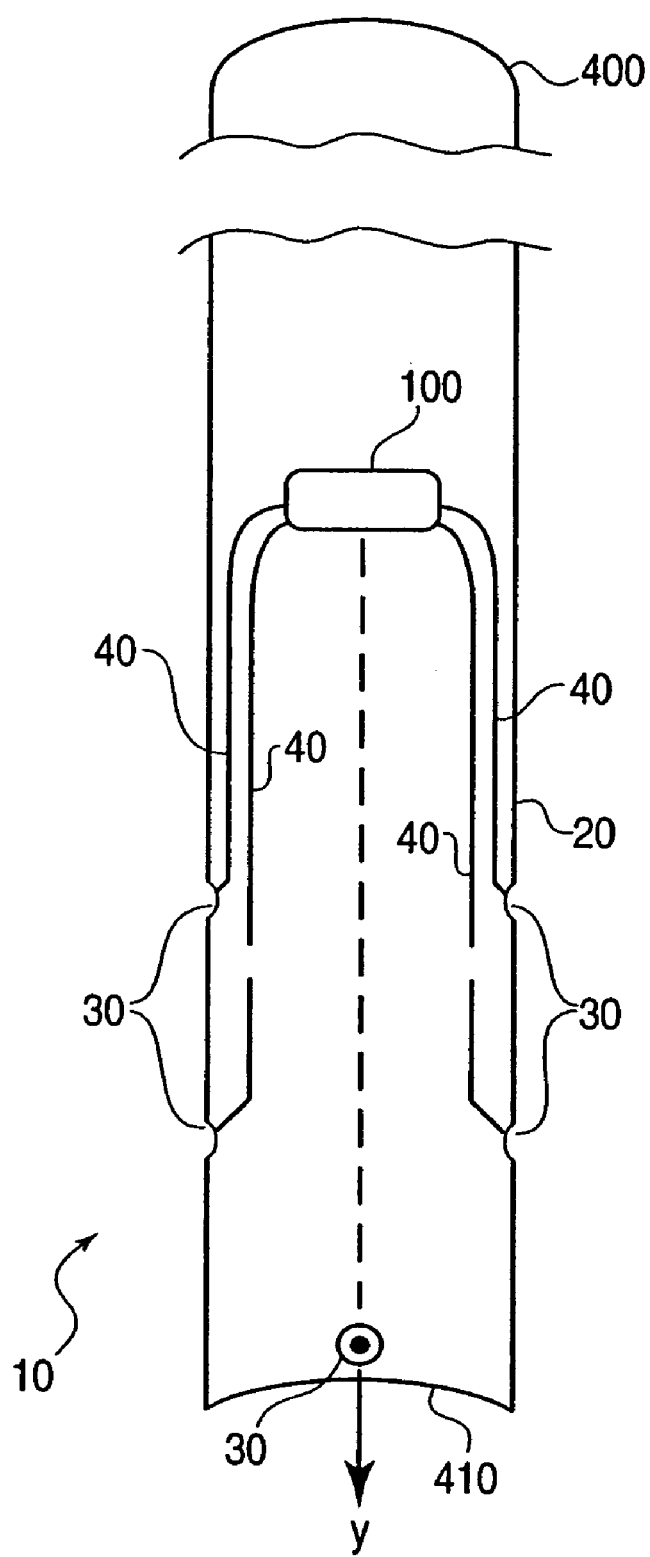
FIG. 3 is a partial interior view of an embodiment of a device according to the present invention.

With respect to general features and aspects of device 10 itself, referring to FIG. 3, device 10 includes a body 20 having a proximal end 400 and a distal end 410 and defines a plurality of ports 30 along the longitudinal axis y thereof between proximal end 400 and distal end 410. Device 10 also includes a plurality of delivery structures 40 that are insertable within body 20. In the case of electrical stimulation, delivery structures 40 may either be leads that are electrically conductive and function as electrodes or delivery structures 40 may be leads having delivery elements 50, which are electrode, disposed thereon. In the case of chemical stimulation, delivery structures 40 are catheters that define delivery elements 50, which are drug ports.

Figure 4A:
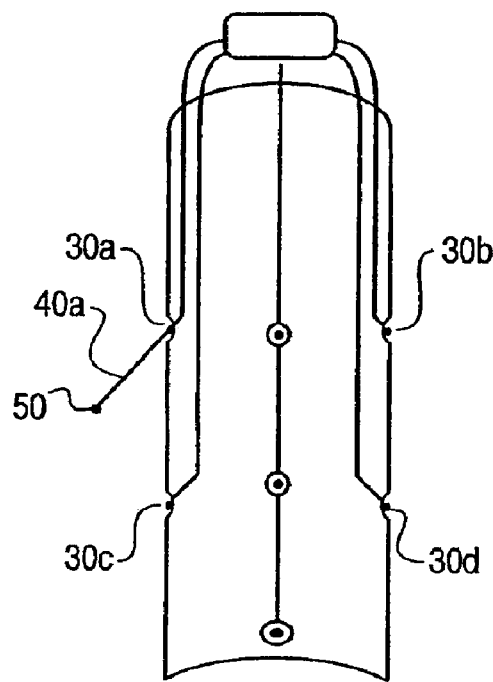
FIGS. 4A-4D depict alternative deployments of a device according to the present invention.
Figure 4B:
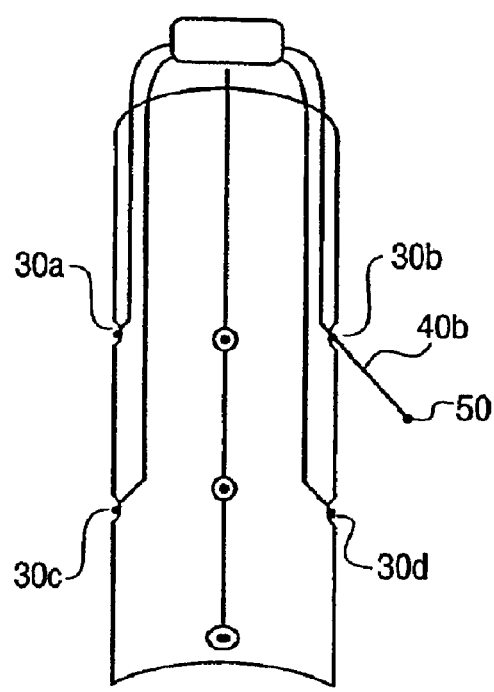
Figure 4C:
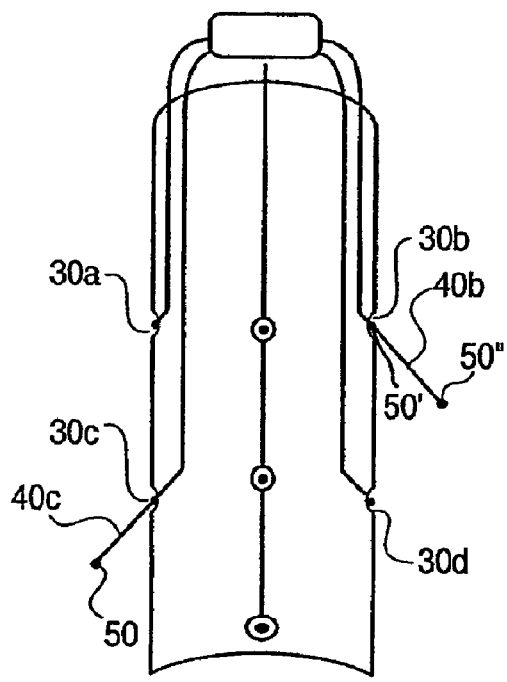
Figure 4D:
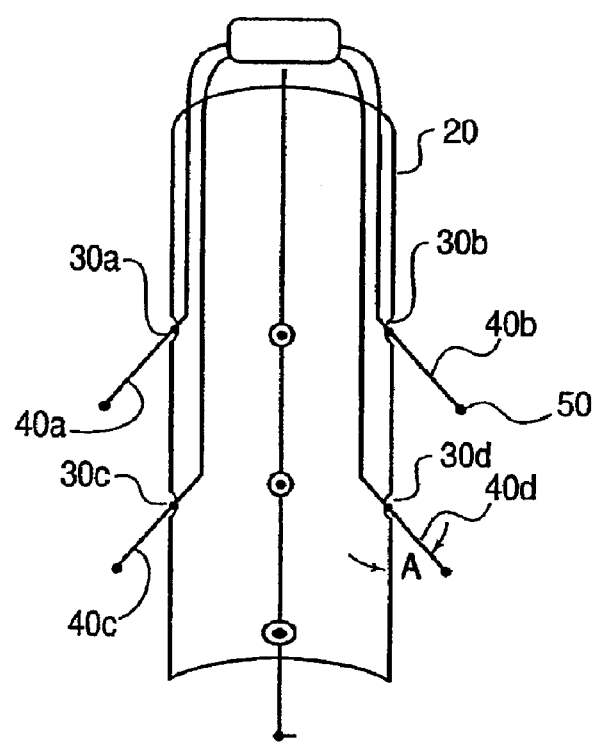

A control mechanism 100 is in communication with the plurality of delivery structures 40 to independently move each of the plurality of delivery structures 40 through a respective one of the plurality of ports 30 with respect to each other of the plurality of delivery structures 40. The ability of each delivery structure 40 to be independently moveable through a respective port 30 allows each delivery structure 40 to be selectively advanced and retracted through the respective port 30 independent of the movement of another delivery structure 40. Such independent moveability of each delivery structure 40 consequently allows a practitioner to modify the locus of stimulation in a multitude of directions and to increase or decrease the volume of neural tissue to be stimulated, in part, as a function of the number of delivery structures 40 advanced. For example, as illustrated in FIG. 4A, if only the neural tissue adjacent to port 30a is desired to be stimulated then delivery structure 40a can be solely advanced through port 30a. As illustrated in FIG. 4B, if it is determined that such stimulation is inefficacious or produces ill side effects, and the locus of stimulation is desired to be redirected to the neural tissue adjacent port 30b then delivery structure 40a can be retracted through port 30a and delivery structure 40b can be solely advanced through port 30b. Alternatively, as illustrated in FIG. 4C, if both the neural tissue adjacent to port 30c and 30b are desired to be stimulated, then delivery structure 40c and delivery structure 40b can both be advanced through respective ports 30c and 30b. Furthermore, as illustrated in FIG. 4D, if a greater volume of neural tissue is desired to be stimulated, such as the neural tissue adjacent to each port 30a-d, then delivery structures 40a-d can all be advanced through ports 30a-d. The present invention contemplates any combination of independent movement of delivery structures 40 depending on the location and volume of the particular neural tissue site(s) desired to be stimulated. All these positional readjustments can be made by advancing or retracting the desired delivery structure 40 or the desired combination of delivery structures 40 without having to extend or retract the overall position of device 10, although device 10 is capable of such a positional readjustment.

Figure 5:
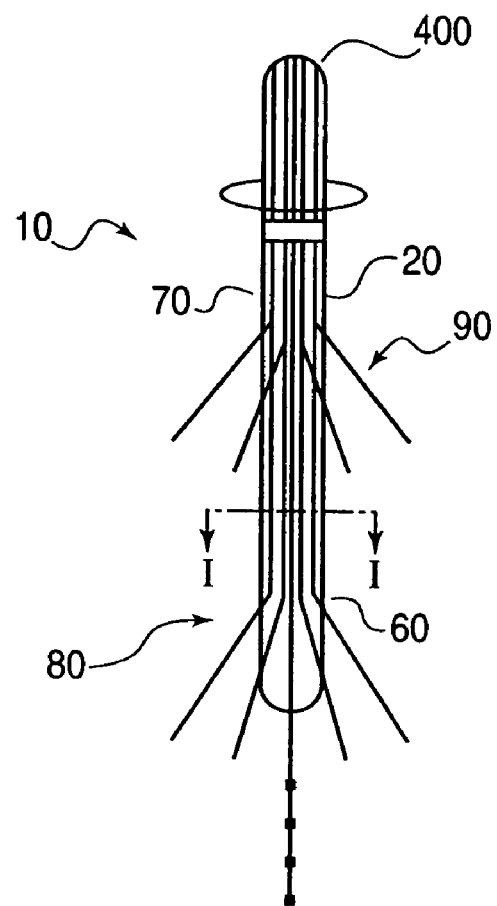
FIG. 5 is a schematic view of an alternative embodiment of a device according to the present invention.
Figure 6:
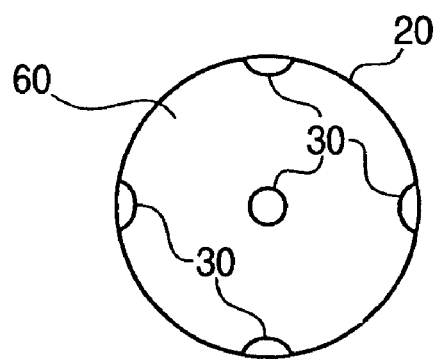
FIG. 6 is a cross-sectional view of the device of FIG. 5 along lines I-I.
Figure 7:
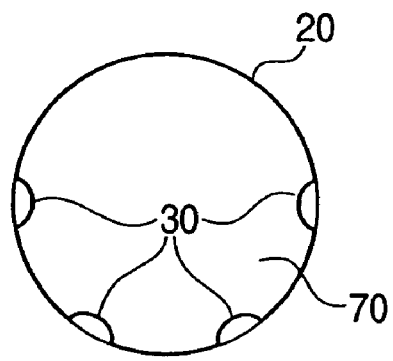
FIG. 7 is a top plan view of an alternative embodiment of a device according to the present invention.

Although the present invention envisions any arrangement of ports 30 along the longitudinal axis y, referring to FIG. 5-7, in a preferred embodiment of the present invention, device 10 includes a first portion 60 containing a plurality of ports 30 and a second, different portion 70 containing a plurality of ports 30. Referring to FIG. 6 first portion 60 and second portion 70 may each contain a plurality of ports 30 arranged annularly in a plane transverse to longitudinal axis y of body 20 (first portion 60 only shown). A first set 80 and a second set 90 of a plurality of delivery structures 40 are, in turn, extendable through the respective plurality of ports 30. Although first portion 60 and second portion 70 may contain any number of ports, each port separated by any number of degrees, in a preferred embodiment, first portion 60 and second portion 70 have four ports each and the ports are situated 90 degrees apart from each other in the same annular plane. Referring to FIG. 7, first portion 60 and second portion 70 may alternatively contain a plurality of ports 30 arranged semi-annularly about a plane transverse to the longitudinal axis y of body 20 (second part 70 only shown.). A first set 80 and a second set 90 of a plurality of delivery structures 40 are, in turn, extendable, through the respective plurality of ports 30 so that each the first set 80 and the second set 90 extend semi-annularly around body 20. In such as embodiment, first portion 60 and second portion 70 are capable of being rotated about axis y to reposition the first set 80 and second set 90 to a different neural tissue site located on the same annular plane if necessary. Although first portion 60 and second portion 70 may contain any number of ports, each port separated by any number of degrees, in a preferred embodiment, first portion 60 and second portion 70 have four ports each and the ports are situated 45 degrees apart from each other in the same annular plane.

Notwithstanding whether first portion 60 and second portion 70 contain ports 30 arranged annularly or semi-annularly, a control mechanism 100 is associated with first set 80 and second set 90 to independently move the plurality of delivery structures 40 of first set 80 and second set 90. The present invention contemplates any combination of independent movement to selectively stimulate the desired region of neural tissue. For example, each of the plurality of delivery structures 40 of first set 80 may be independently moveable with respect to each other of the plurality of delivery structures 40 of first set 80 and/or second set 90 and each of the plurality of delivery structures 40 of second set 90 may be independently moveable with respect to each other of the plurality of delivery structures 40 of second set 90 and/or first set 80. In an alternative embodiment, first set 80 is collectively moveable independent of the movement of second set 90 and second set 90 is collectively moveable independent of the movement of first set 80. Specifically, first set 80 may be collectively advanced to stimulate neural tissue adjacent to the first annular portion 60 while second set 90 may be collectively retracted within body 20. If it is desired to redirect stimulation to the area of neural tissue adjacent to the second annular portion 70, second set 90 may be collectively advanced through the respective plurality of ports 30 and first set 80 may be collectively retracted into body 20. If it is desired to stimulate both the area of neural tissue adjacent to the first annular portion 60 and the second annular portion 70, both first set 80 and second set 90 may be advanced through the respective plurality of ports 30.

Although first and second portions 60 and 70 are not limited to a particular relative arrangement, preferably second portion 70 is between first portion 60 and proximal end 400 of body 20. Furthermore, although the distance between first portion 60 and second portion 70 may depend on the particular application of device 10, preferably such distance is between 5 to 10 millimeters. More preferably, such distance is between 4 to 5 millimeters. Moreover, although first portion 60 and second portion 70 may include any number of ports, preferably both portions collectively define eight ports. Additionally, the present invention also contemplates embodiments of device 10 where body 20 only includes a first portion 60 or a second portion 70, notwithstanding whether first portion 60 or second portion 70 define an annular or semi-annular arrangement of a plurality of ports 30.

The present invention also contemplates an arrangement of the plurality of ports 30 and therefore a plurality of delivery structures 40 individually moveable through the respective plurality of ports 30 that are tailored for the particular target site desired to be stimulated. In other words, in this embodiment, the number, arrangement, and distance between ports 30 are a function of the target site desired to be stimulated. For example, body 20 may define five ports 30 spaced 20 degrees apart from each other and therefore contain five delivery structures 40, which when in an extended position, are 20 degrees apart from each other to stimulate a particular target site for which this arrangement of delivery structures is most efficacious. For another target site, body 20 may define 3 ports 30 spaced 5 degrees apart from each other and therefore contain three delivery structures 40, which when in an extended position, are 5 degrees apart from each other to effectively stimulate the target site.

Figure 8:
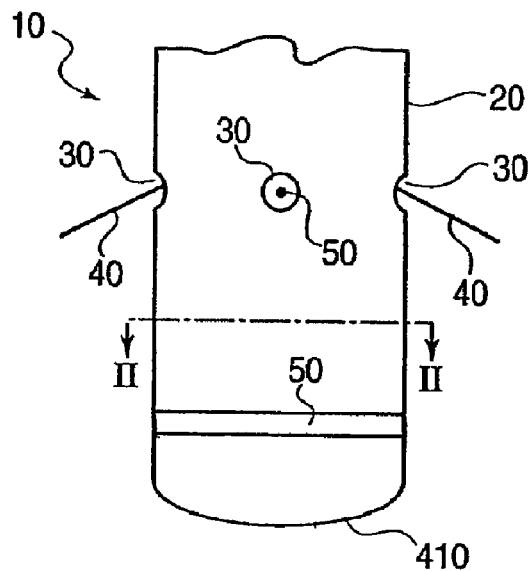
FIG. 8 is a partial side view of an alternative embodiment of a device according to the present invention.
Figure 9:
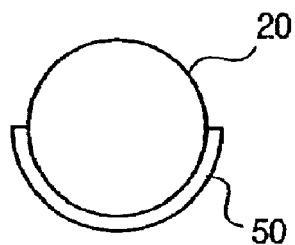
FIG. 9 is a cross-sectional view of the device of FIG. 8 along lines II-II.
Figure 10:
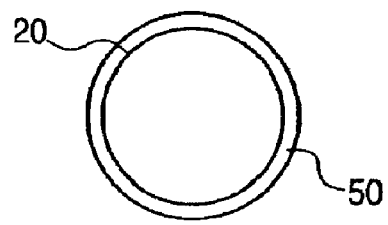
FIG. 10 is a cross-sectional view of an alternative embodiment of a device according to the present invention.
Figure 11:
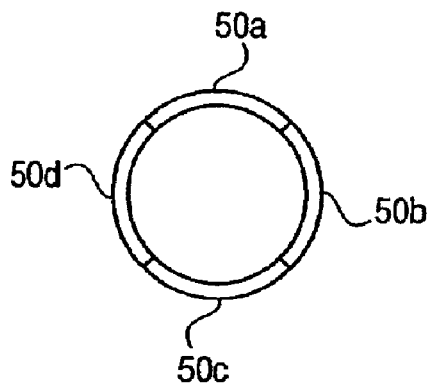
FIG. 11 is a cross-sectional view of an alternative embodiment of a device according to the present invention.

Referring to FIG. 8, in another embodiment of the present invention, device 10 comprises a body 20 having a proximal end (not shown) and a distal end 410 and defines a plurality of ports 30 between proximal end and distal end 410. Although the plurality of ports 30 are illustrated as being annularly arranged on the same plane, the present invention contemplates any other arrangement of the plurality of ports 30 as well as including a semi-annular arrangement on the same plane. Device 10 further includes a plurality of delivery structures 40 that are each independently moveable through a respective one of the plurality of ports 30 with respect to each other of the plurality of delivery structures 40. In this embodiment, device 10 further includes a delivery element 50, which can either be a drug port or electrode, disposed on body 20. Although delivery element 50 may be located anywhere in relation to the plurality of ports 30, in a preferred embodiment, delivery element 50 is located between the plurality of ports 30 and distal end 410 of body 20. Referring to FIGS. 9 and 10, delivery element 50 may extend approximately 360 degrees about body 20, as illustrated in FIG. 10, or less than 360 degrees about body 20, as illustrated in FIG. 9 (showing delivery element 50 extending approximately 180 degrees about body 20). Furthermore, in the case of electrical stimulation where delivery element 50 is an electrode, delivery element 50 may be uniformly powerable such that the entire delivery element 50 is a continuous delivery element that delivers electrical stimulation of uniform pulse, frequency, voltage and other pulsing parameters. Alternatively, as illustrated in FIG. 11, delivery element 50 may be divided into two or more segments (four segments 50a-d illustrated) that are each selectively powerable such that each segment 50a-d can be powered to initiate, stop, increase, or decrease pulsing parameters independent of each other segment 50a-d. Segments 50a-d may extend about body 20 by substantially equal number of degrees or by different number of degrees. In a preferred embodiment, electrode 50 is divided into three segments 50a-c, each extending approximately 120 degrees about body 20.

Figure 12:
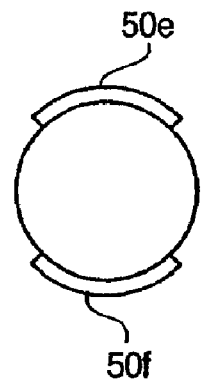
FIG. 12 is a cross-sectional view of an alternative embodiment of a device according to the present invention.
Figure 13:
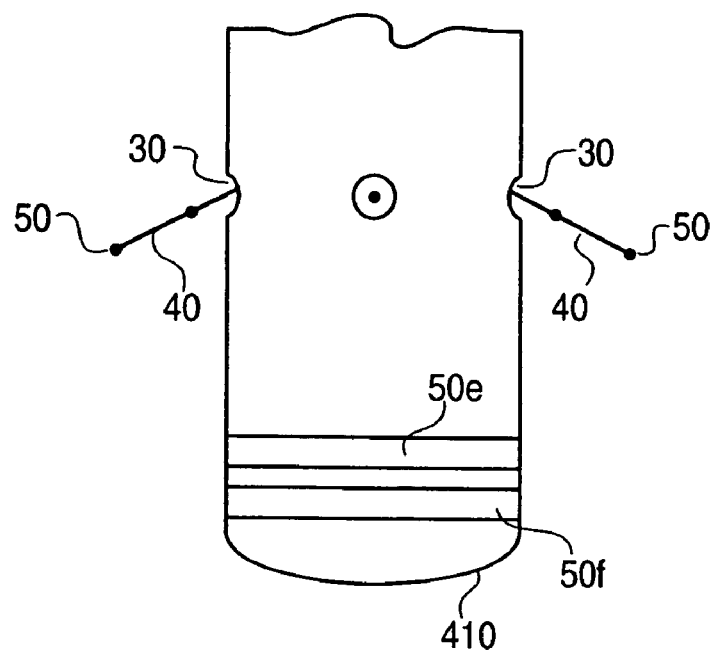
FIG. 13 is a partial side view of an alternative embodiment of a device according to the present invention.
Figure 14:
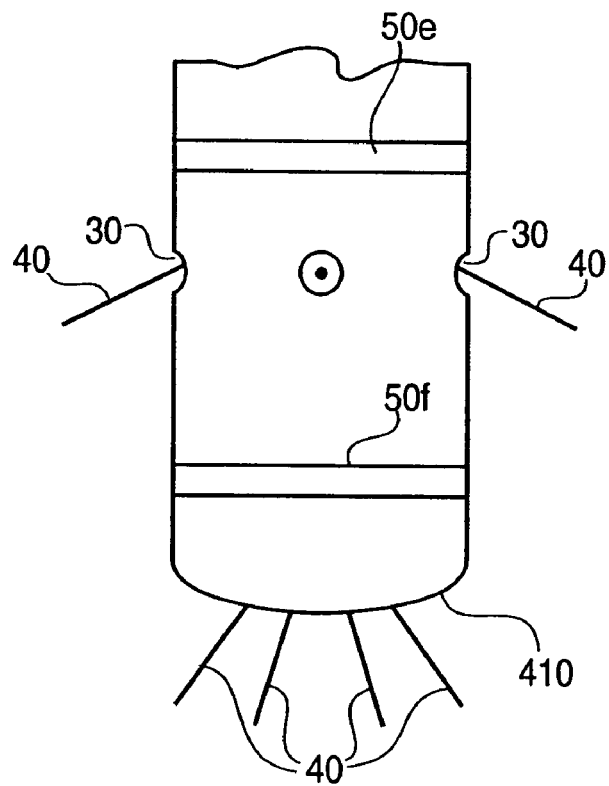
FIG. 14 is a partial side view of an alternative embodiment of a device according to the present invention.

Referring to FIG. 12, in another embodiment of the present invention, device 10 includes two delivery elements 50e and 50f, that are spatially distinct and, in the case of electrical stimulation, are preferably electrically distinct from each other. Although delivery elements 50e and 50f are illustrated as residing on the same annular plane, they can be disposed anywhere on body 20. For example, as seen in FIG. 13, delivery elements 50f is located between delivery element 50e and distal end 410 of body 20. Referring to FIG. 14, in another embodiment, delivery element 50e is located between a proximal end (not shown) of body 20 and the plurality of ports 30 and delivery element 50f is located between the plurality of ports 30 and distal end 410 of body 20.

In all the above described embodiments, device 10 includes at least one delivery element 50 disposed on body 20, and body 20 may define at least one port, and preferably a plurality of ports at distal end 410 of body 20, as illustrated in FIG. 14. Furthermore, body 20 may include three, four, or any number of additional delivery elements 50 disposed on body 20, any one of which or all of which are selectively powerable. It will be readily appreciated by one skilled in the art that delivery elements 50 can vary circumferentially in height, width, axial spacing and/or shape to provide the desired field of use. In addition, although delivery elements 50 are illustrated as being supported by or resting on body 20, delivery elements 50 may alternatively be embedded into, formed integrally with, or otherwise supported on body 20. Furthermore, body 20 may define any arrangement or number of the plurality of ports 30 that are located superiorly or inferiorly to delivery element 50. In a preferred embodiment, body 20 defines an annular arrangement of ports 30 about a plane transverse to the longitudinal axis y of device 20 as seen in FIGS. 8, 13, and 14.

Figure 15:
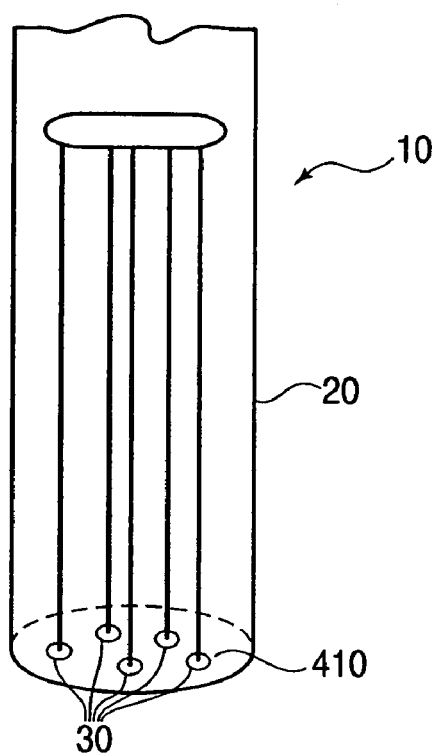
FIG. 15 is a partial interior view of an alternative embodiment of a device according to the present invention.
Figure 16:
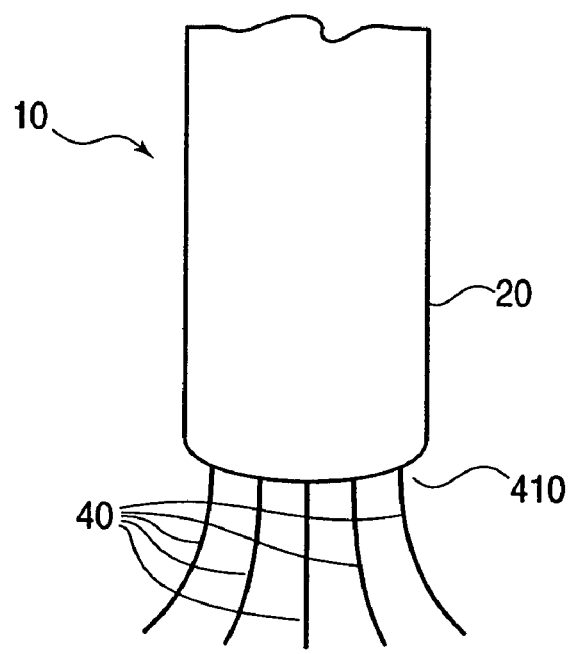
FIG. 16 is a partial side view of the device of FIG. 15.

Referring to FIGS. 15 and 16, in an alternative embodiment of the present invention, device 10 includes a body 20 having a proximal end (not shown) and a distal end 410, and defining a first plurality of ports 30 at distal end 410. Body 20 further includes a first plurality of delivery structures 40 that are each independently moveable through a respective one of the first plurality of ports 30 with respect to each other of the first plurality of delivery structures 40. Referring to FIG. 16, although delivery structures 40 are illustrated as having an arcuate configurations, they may also have a non-arcuate configuration, such as a linear configuration. Furthermore, in an alternative embodiment, device 10 further includes a second plurality of ports 30 located between a proximal end and distal end 410 and a second plurality of delivery structures 40 that are extendable through a respective one of the second plurality of ports 30. The second plurality of delivery structures 40 may also be independently moveable with respect to each other of the second plurality of delivery structures 40 and/or each of the first plurality of delivery structures 40. Moreover, additional delivery elements 50 may be disposed on body 20 as described in more detail above.

Figure 17A:
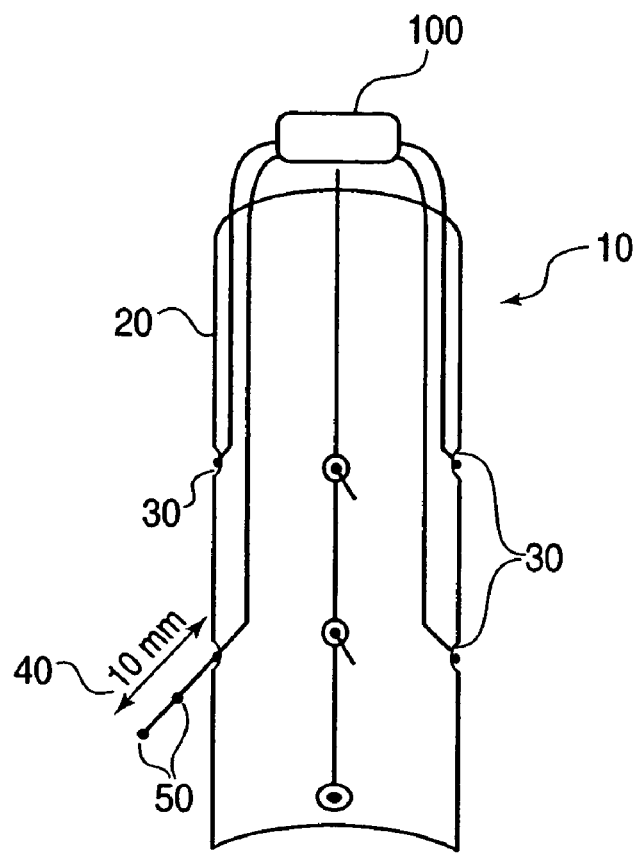
FIGS. 17A-17B depict alternative deployments of a device according to the present invention.
Figure 17B:
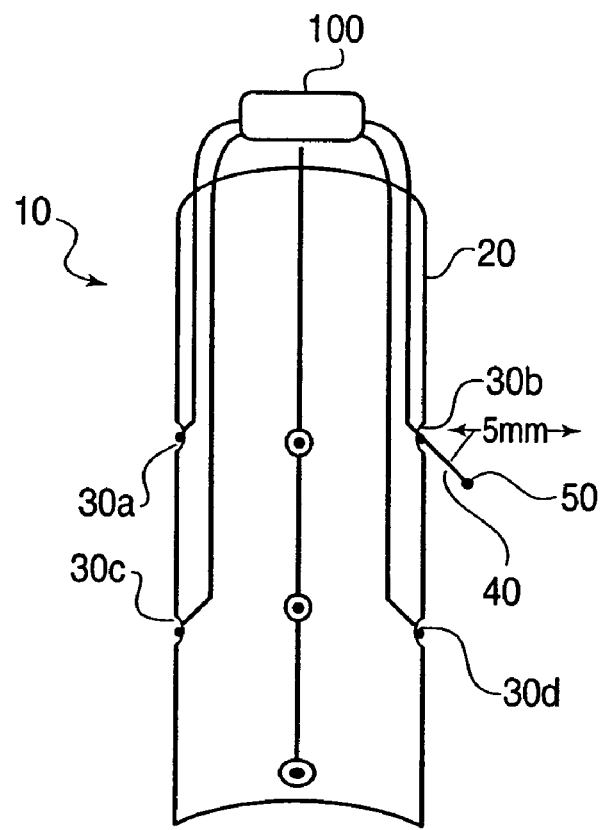

In addition to the above-mentioned embodiments modulating the direction in which delivery structures 40 can extend from body 20, the present invention contemplates alternative embodiments of device 10 that also permit modulating the distance delivery structures 40 can extend from body 20. In particular, the plurality of delivery structures 40 may be flush with port 30, as illustrated in FIG. 3, or advanced varying distances away from body 20 as illustrated in FIG. 17. Preferably, delivery structures 40 can each be advanced between about 1 millimeters and about 10 millimeters away from port 30 of body 20 to provide stimulation to up to approximately 2 $cm^3$ of neural tissue. Therefore, depending on the distance between the desired site of stimulation and body 20, a delivery structure 40 can be fully advanced through a respective port 30, as illustrated in FIG. 17A or only partially advanced as illustrated in FIG. 17B. Thus, if a practitioner initially stimulates a first neural tissue site and then desires to stimulate a second, different neural tissue site located further away from device 10, the practitioner simply adjusts the distance the delivery structure is extended through port 30 without having to shift the overall position of device 10, although device 10 is capable of such a positional readjustment.

In addition to modulating the direction and/or the distance each delivery structure 40 can extend, alternative embodiments of device 10 also permit modulating the degree of stimulation each delivery structure 40 can deliver. In such embodiments, delivery structures 40 have delivery elements 50 disposed thereon, and delivery elements 50 are adjustably powerable electrodes. For example, the pulsing parameters of delivery elements 50 may be adjusted to initiate, stop, increase, or decrease the pole combinations, energy, amplitude, pulse width, waveform shape, frequency, and/or voltage or any other pulsing parameter known to one of skill in the art to adjust the degree of stimulation delivered thereby. In a preferred embodiment, each delivery element 50 of each delivery structure 40 is selectively powerable such that the pulsing parameters of a delivery element 50 can be adjusted independent of the pulsing parameters of another delivery element 50.

Figure 1:
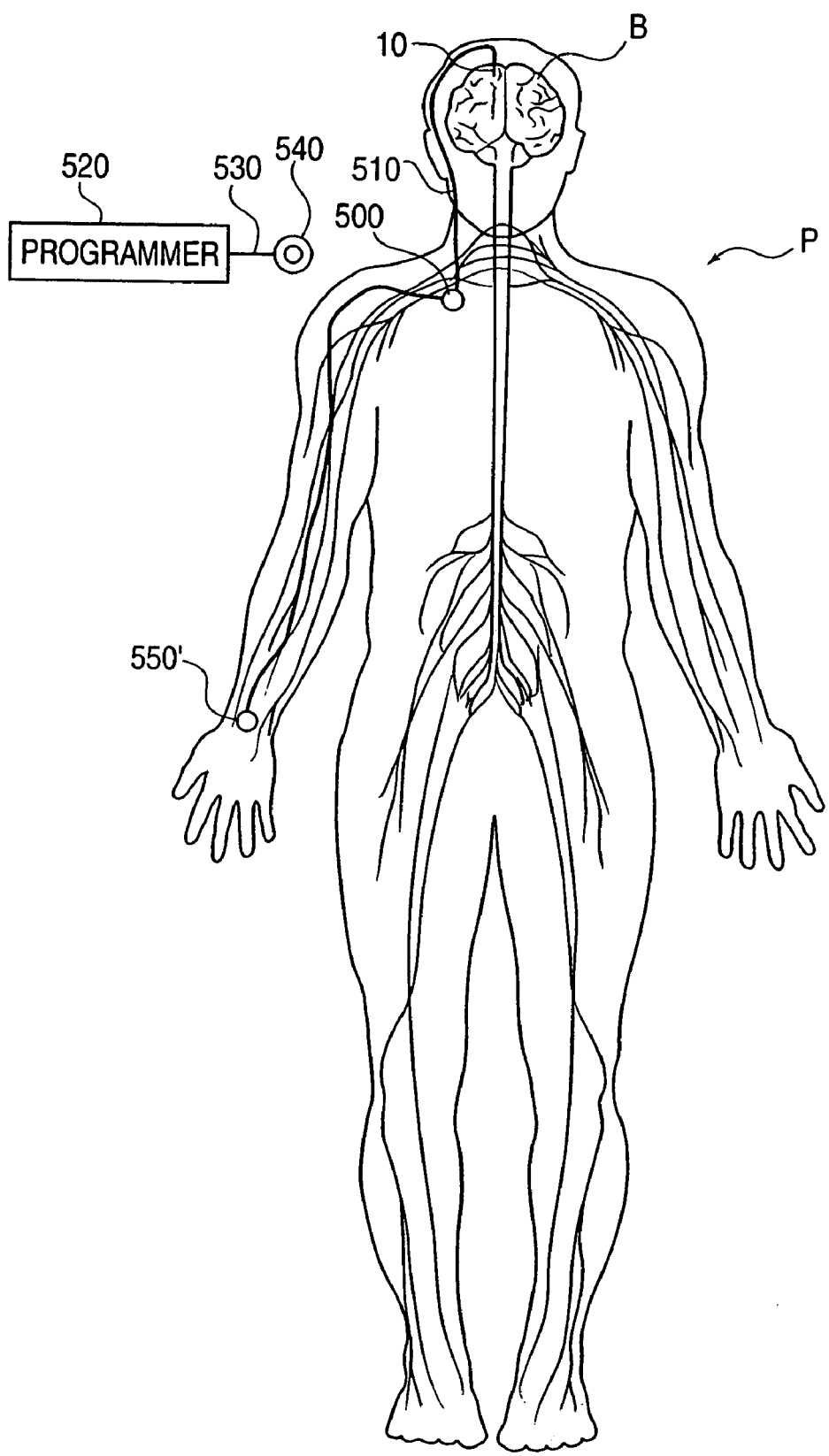
FIG. 1 is a diagrammatic view of a patient in which an embodiment of a device according to the present invention has been implanted.
Figure 2:
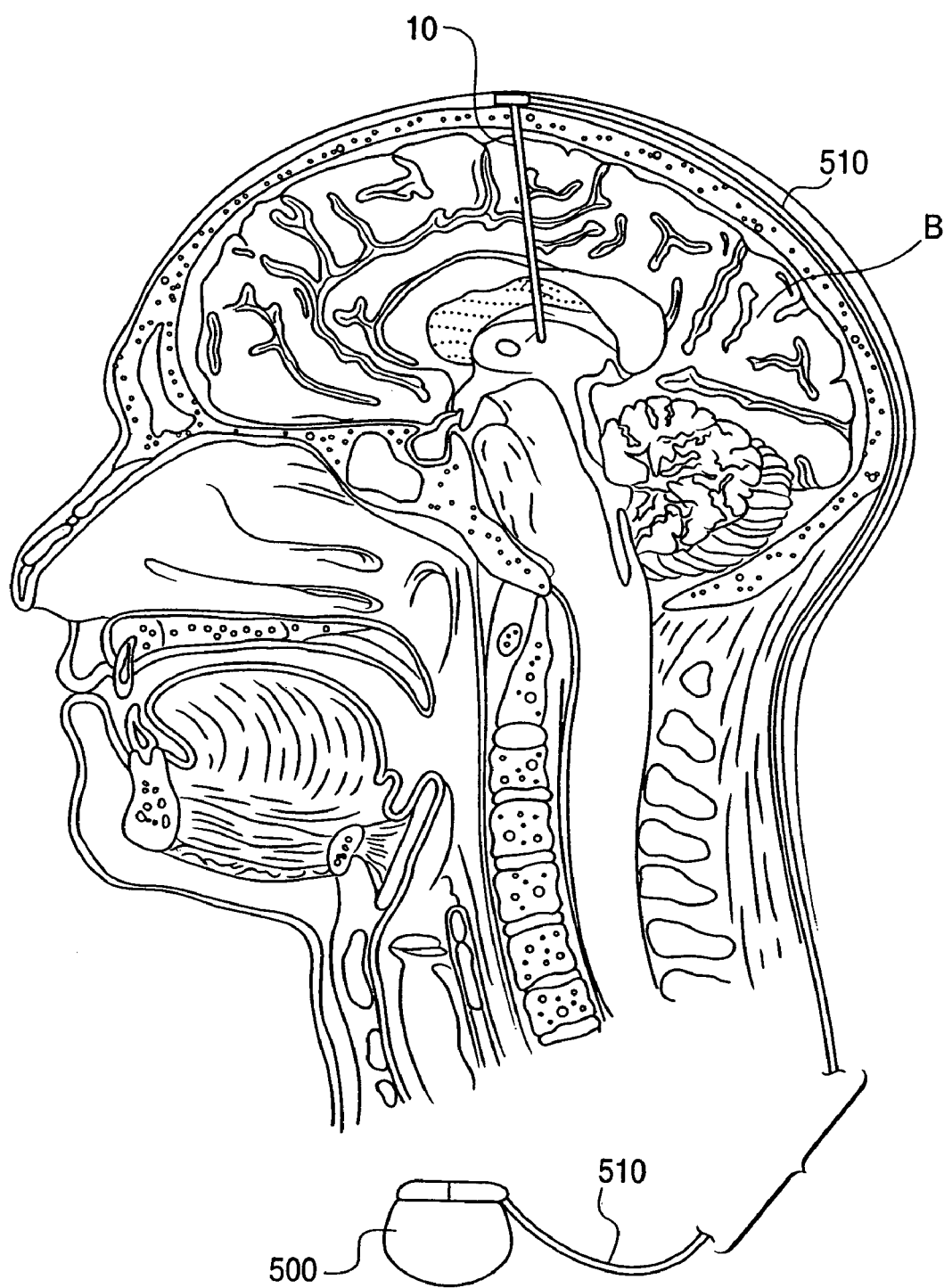
FIG. 2 is a cross-sectional view of the brain showing one placement of an embodiment of a device according to the present invention.

Referring to FIG. 1, in such an embodiment, the selective powerability over each delivery element 50 may be achieved by employed a system including a programmer 520 coupled via a conductor 530 to a telemetry antenna 540. The programmer 520 is capable of sending signals via the telemetry antenna 540 to control the electrical signal delivered to delivery elements 50 and, optionally, to control mechanism 100, in embodiments where control mechanism 100 is remotely operated. Such a system permits the selection of various pulse output options after device 10 is implanted using telemetry communications. The present invention also contemplated radio-frequency systems to selectively power delivery elements 50.

Referring to FIG. 1, in such an embodiment, the selective powerability over each delivery element 50 may be achieved by employing a system including a programmer 520 coupled via a conductor 530 to a telemetry antenna 540. The programmer 520 is capable of sending signals via the telemetry antenna 540 to control the electrical signal delivered to delivery elements 50 and, optionally, to control mechanism 100, in embodiments where control mechanism 100 is remotely operated. Such a system permits the selection of various pulse output options after device 10 is implanted using telemetry communications. The present invention also contemplates radio-frequency systems to selectively power delivery elements 50.

As will be understood by one of skill in the art, the independent powerability of delivery elements 50 also provides a practitioner with another means of modify modifying or steering the direction of stimulation, as the locus of stimulation can be selectively adjusted to precisely target portions of neural tissue to achieve the desired therapy. For example, referring to FIG. 4C, electrode 50' may be powered to stimulate an area adjacent thereto while the signal to electrode 50" may be substantially minimized to reduce or stop stimulation to an area adjacent to electrode 50'". Because the locus of stimulation can be selectively adjusted and/or steered in this embodiment of device 10, neural tissue can be precisely targeted to achieve the desired therapy. Other or additional means of selectively steering electrical stimulation may also be utilized in the present invention, such as the methods described in U.S. Pat. No. 5,713,922, which is incorporated by reference herein.

With respect to the ability of each delivery structure 40 to be independently moveable through a respective port 30, such independent moveability is effectuated by a control mechanism 100 that is capable of independently advancing and retracting a delivery structure 40 through a respective port 30 of body 20. As illustrated in FIGS. 3, 4, and 17, in one embodiment, control mechanism 100 includes a gear and clutch assembly that may be disposed within body 20 and is similar to the gear and clutch assemblies described in U.S. Pat. Nos. 5,606,975 and 5,034,004, both of which are incorporated herein by reference. In a preferred embodiment, the gear and clutch assembly is motorized, and the motor may be located at the burr hole via a spool magnetically or electrically activated via a radio-frequency coil or an internal power source linked to the burr hole or the implantable signal generator or radio-frequency receiver. The power for the moving of delivery structure 40 originates from a gear and clutch system that may be controlled by micro-electrical mechanical systems as part of the implantable signal generator and device 10, which is moved when the clutch is engaged.

Figure 18:
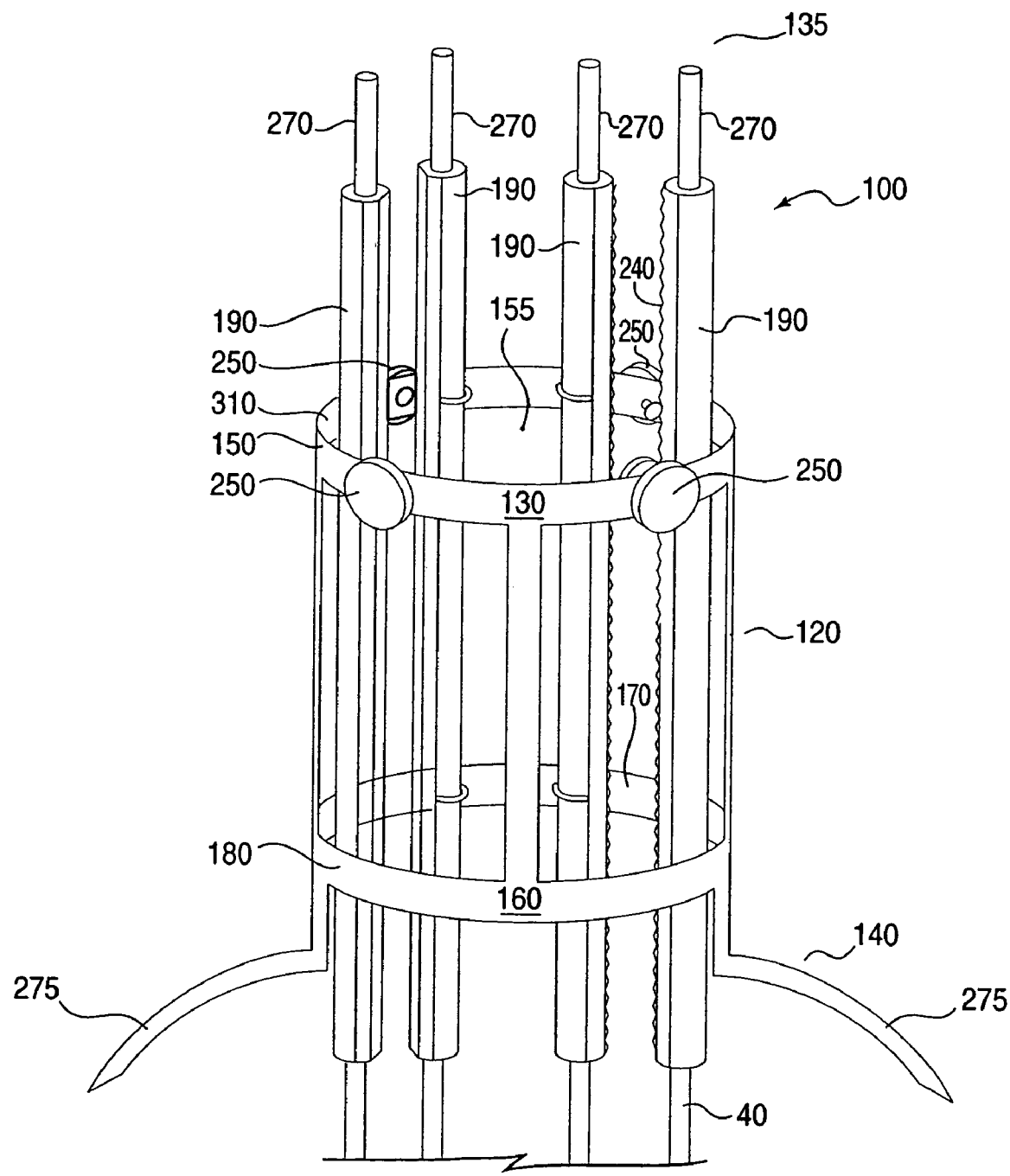
FIG. 18 is a perspective view of a control mechanism according to the present invention.

Referring to FIG. 18, in an alternative embodiment, control mechanism 100 includes a rack and pinion gearing mechanism that is capable of being manually operated. In particular, in this embodiment, control mechanism 100 includes a carrier 120, a plurality of shafts 190 insertable within carrier 120, each of the plurality of shafts capable of engaging at a distal end thereof a respective one of a plurality of delivery structures 40, and a plurality of drivers 250 each associable with a respective shaft 190 such that upon manipulation of a driver 250, the respective delivery structure 40 will endwise be advanced or retracted through body 20.

Figure 19:
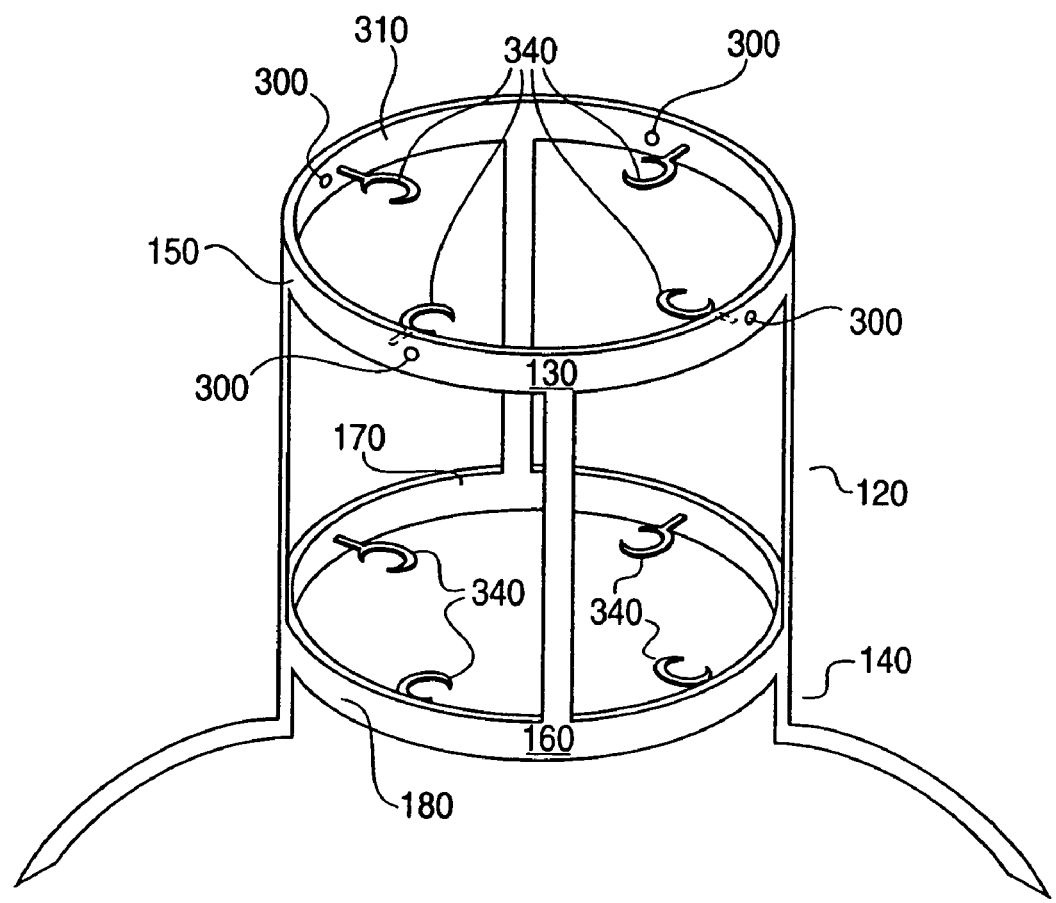
FIG. 19 is a perspective view of a control mechanism according to the present invention.
Figure 20:
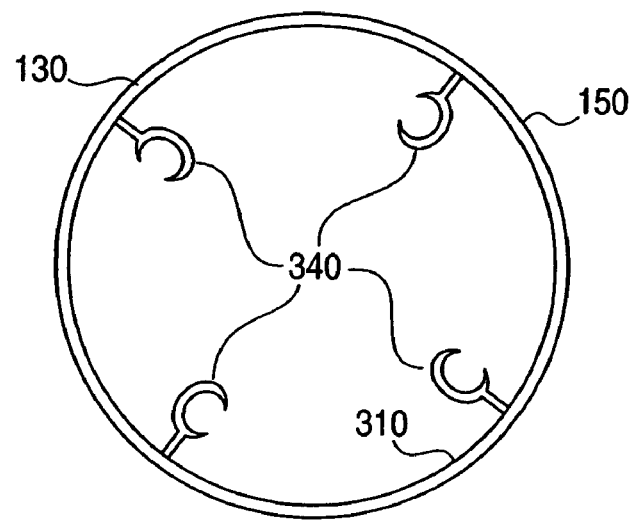
FIG. 20 is a top view of a control mechanism according to the present invention.

In particular, carrier 120 of control mechanism 100 has a proximal end 135, a distal end 140 optionally defining a set of securement arms 275, and a lumen 155 extending therethrough. Carrier 120 further includes a first support portion 130 having an inner surface 310 and an outer surface 150 and/or a second support portion 160 having an inner surface 170 and an outer surface 180. As illustrated in greater detail in FIGS. 19 and 20, extending from or extensions of inner surface 310 and inner surface 170 are a plurality of clamping members 340 each configured to securely engage a respective one of a plurality of shafts 190 insertable in lumen 155. Although preferably, carrier 120 includes both a first support portion 130 and a second support portion 160 to secure shafts 190 to carrier 120, carrier 120 may include only a first support portion 130 or a second support portion 160. Furthermore, other means of securing shafts 190 to carrier 120 will be readily appreciated by one of skill in the art and are therefore within the scope of the present invention. Referring to FIG. 19, one of first portion 130 and second portion 160 preferably defines an annular arrangement of a plurality of apertures 300 about a plane transverse to axis y, each aperture 300 configured to accommodate a driver 250. Furthermore, referring to FIGS. 18 and 19, distal end 140 of carrier 120 may define securement arms 275 configured to secure carrier 120 atop a burr hole in which carrier 120 may be placed. Alternatively, carrier 120 may be configured to securely fit in a burr hole without the use of securement arms 270. Accordingly, other means of securing carrier 120 in a desired region will be readily appreciated by one of skill in the art and are therefore within the scope of the present invention.

Figures 21, 22:
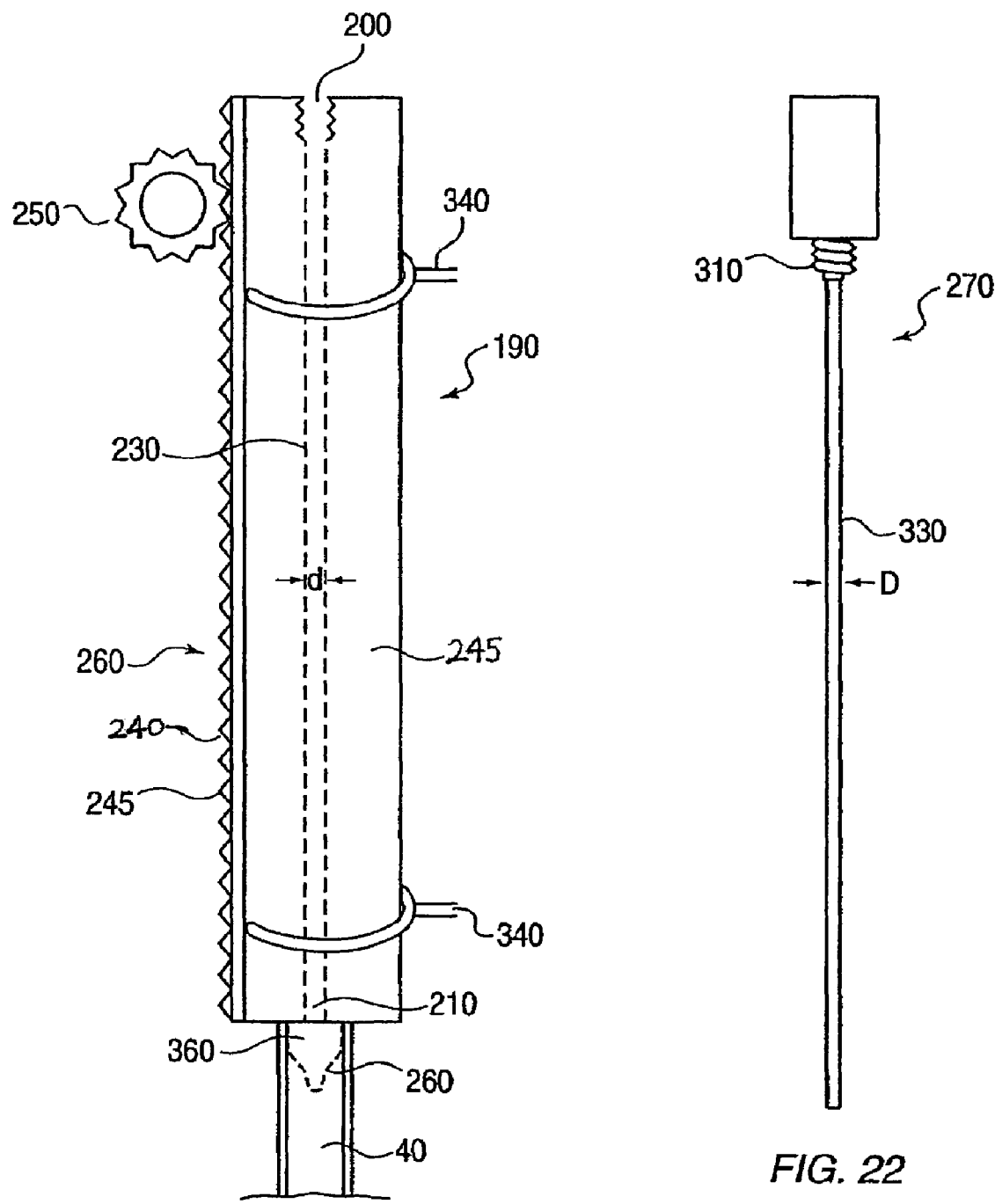
FIG. 21 is a side view of a component of a control mechanism according the present invention.
FIG. 22 is a side view of a component of a control mechanism according to the present invention.

Referring to FIG. 21, each shaft 190 has a channel 230 extending therethrough to accommodate a stylet 270, such channel 230 having a proximal end 200 and a distal end 210. Shaft 190 further has an outer surface 245 that defines an engaging portion 260. Engaging portion 260 may be a substantially planar surface from which a series of axially spaced serrations 240 extend or of which a series of axially spaced serrations 240 are extensions. Alternatively, engaging portion 260 may itself be a series of axially spaced serrations 240 (not shown). A hollow fastener 360 configured to engage a proximal end 260 of a delivery structure 40 may be attached to or be defined by shaft 190 about a distal end 210 of channel 230. Alternatively, distal end 210 of channel 230 may define an aperture that is configured to engage proximal end 260 of delivery structure 40 (not shown). Fastener 360 or the like can engage proximal end 260 of delivery structure 40 through resistance fitting, a screw-like mechanism, adhesive bonding, or the like. Other means of engaging a delivery structure 40 and other mechanisms by which such engagement is accomplished will be readily appreciated by one of skill in the art and are within the scope of the present invention.

Channel 230 of shaft 190 is also configured to allow a leading end 330 of a stylet 270 to pass therethrough to access and pass through delivery structure 40. Referring to FIGS. 21 and 22, preferably, channel 230 has a diameter d that is only slightly greater than a diameter D of leading end 330 of stylet 270 to prevent lateral displacement of leading end 330 during manipulation of shaft 190. To prevent axial displacement of stylet 270 during advancing movement of delivery structure 40, stylet 270 preferably includes a limit stop 310 configured to associate with proximal end 200 of channel 230 through resistance fitting, a screw-like mechanism, adhesive bonding or the like.

Figure 23:
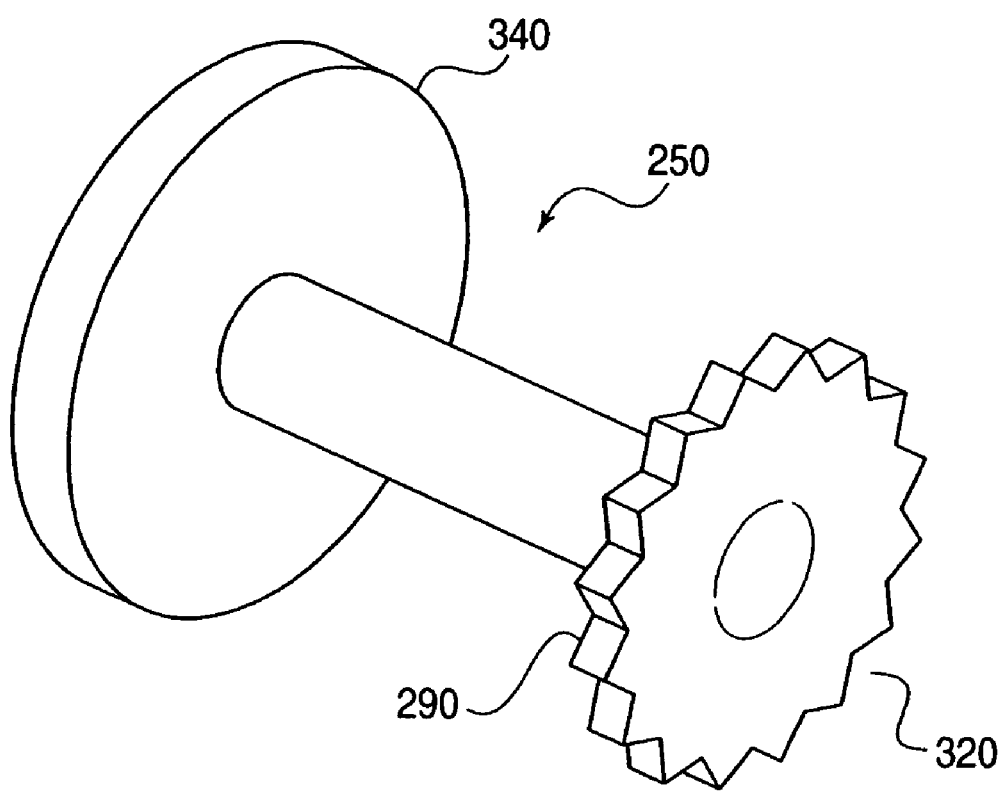
FIG. 23 is a perspective view of a component of a control mechanism according to the present invention.

Control mechanism 100 further includes a plurality of drivers 250 each associable with a respective shaft 190 such that upon manipulation of a driver 250, the corresponding delivery structure 40 will endwise be advanced or retracted through body 20. Referring to FIG. 23, driver 250 includes a handle 340 at a proximal end thereof and a gear 320 at a distal end thereof. Gear 320 defines external threading 290 that is configured for threadable engagement with serrations 240 of shaft 190 such that manipulation of a driver 250 results in axial movement of the corresponding shaft 190 and therefore axial movement of the corresponding delivery structure 40 attached about the distal end 210 of channel 230 of shaft 190. Depending on the rotational movement provided to the driver 250 (i.e. whether by turning handle 340 in a clockwise or counter-clockwise direction), respective delivery structure 40 is retracted or advanced through body 20 and through port 30. Preferably, external threading 290 of driver 250 and serrations 240 of shaft 190 have a cooperative pitch fine enough to allow for precise movement of a delivery structure 40 such that delivery structure 40 can be millimetrically extended and retracted through ports 30. As seen in FIG. 18, gear 320 of driver 250 may access serrations 240 of shaft 190 by passing through apertures 300 of first or second portion 130 and 160 of carrier 120.

Figure 24:
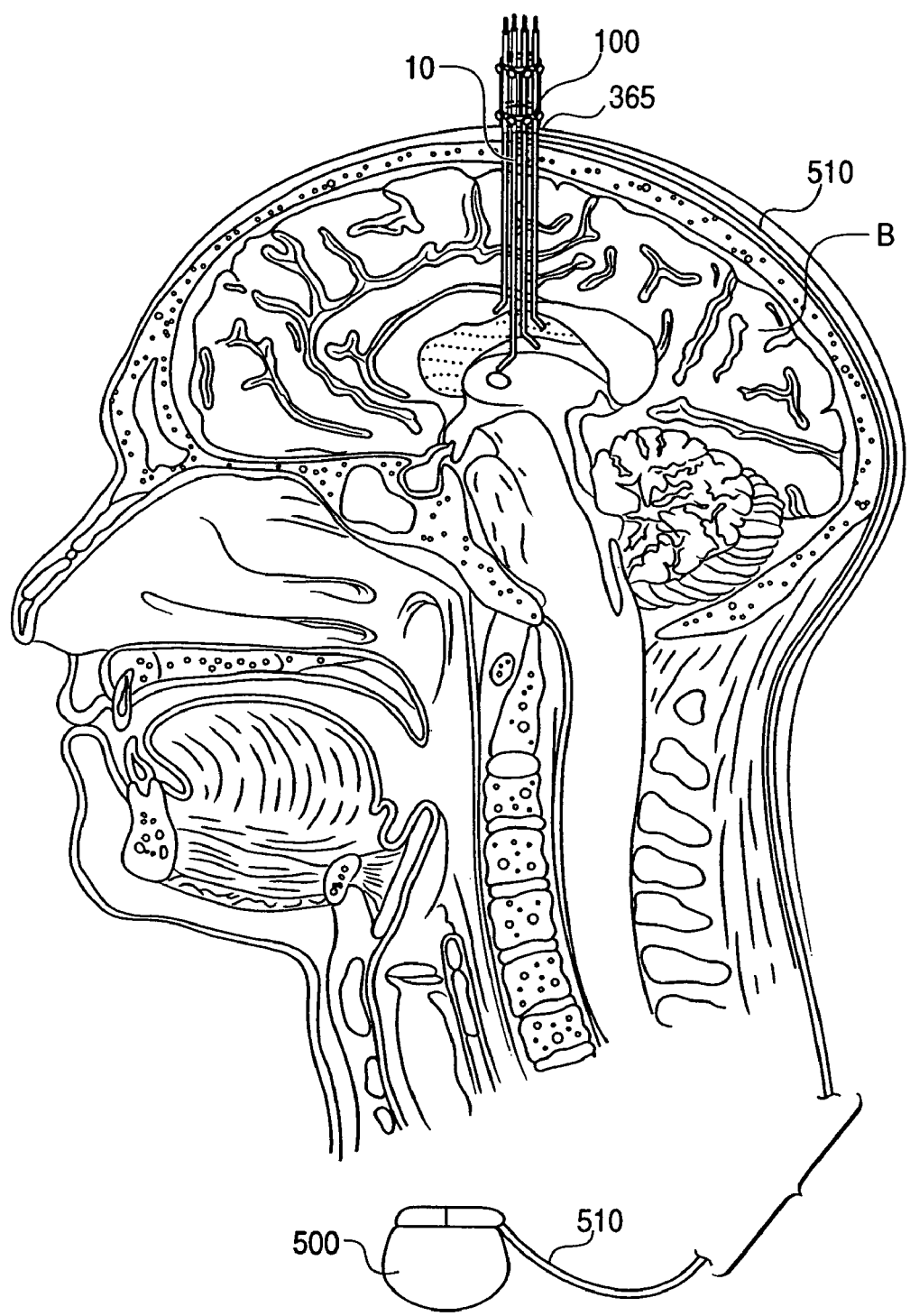
FIG. 24 is a cross-sectional view of a device according to the present invention implanted in the brain of a patient and attached to a control mechanism according to the present invention.

Referring to FIG. 24, with respect to one exemplary use of the above-described control mechanism 100, device 10 is inserted in the brain B and positioned at a neural tissue target site. Proximal ends 260 of each of the plurality of delivery structures 40 are attached to respective fasteners 360 of shafts 190 and carrier 120 is mounted atop a burr hole 365. Preferably, control mechanism 100 is designed to engage a burr hole ring and communicate with a compass mechanism that provides a frame of reference and that is associated with the burr hole ring or associated with control mechanism 100 itself to align control mechanism 100 in the proper reference frame of the stereotactic coordinates setting to actuate independent movement of delivery structures 40 to a desired target site.

The above-mentioned embodiment of control mechanism 100 is only exemplary and several modifications of such mechanism 100 may be made without detracting or departing from the spirit or scope of the present invention. For example, stylet 270 can be designed to engage distal end 210 of channel 230 similar to the engagement of delivery structure 40 with distal end 210 of channel 230 such that shaft 190 need not define channel 230 to accommodate stylet 270. In addition, each delivery structure 40 can superiorly pass through channel 230 and exit proximal end 200 of shaft 190. Furthermore, several (or all) components of carrier 120 can be designed to releasably associate or affixedly associate with their cooperative components. For example, delivery structures 40 can be affixedly associated with distal end 210 of channel 230 or releasably associated with distal end 210 of channel 230. Furthermore, drivers 250 can be releasably insertable through apertures 300 or affixedly insertable through apertures 300. In addition, the shapes of various components of the above-described embodiment of control mechanism 100 are not limited to the illustrated embodiments. For example, although carrier 120 and shaft 190 are illustrated as being cylindrical in shape, carrier 120 and shaft 190 can take on any shape. Also, although the above-described control mechanism 100 may be manually operated, the present invention also contemplates embodiments that are automated.

Furthermore, the above-described control mechanism 100 is by no means the only control mechanism that can by used in the present invention and the present invention contemplates various other forms of control mechanism 100 to actuate movement of delivery structures 40 including plunger or piston assemblies; springs; guide wires; ceramic motors; other linear motion devices, such as linear actuators and linear guides; rotary motion devices that convert rotary motion to linear motion; external remotely operated means such as electromagnetic signals, radio-frequency signals, or telemetry including the methods described in U.S. Pat. No. 6,192,279, which is incorporated by reference herein; or any other means known to one of skill in the art to actuate linear movement of delivery structures 40. Any control mechanism 100 for use with device 10 may be detachably or attachably mounted atop a burr hole 365, secured within a burr hole 365, or placed between the scalp and skull.

With respect to particular details of the present invention, body 20 may be configured in any shape although a preferred shape is tubular. Furthermore, body 20 may be constructed of stainless steel, iridium, titanium, biocompatible plastic or the like. In a preferred embodiment, body 20 is constructed of polyurethane or polypropylene. In order for body 20 to remain associated with delivery structures 40, body 20 may be secured to delivery structures 40 or to control mechanism 100. Body 20 may be secured to delivery structures 40 by a slidable engagement mechanism, such as tracks that have a first side affixed to body 20 and a second opposite side slidably engaged with delivery structures to allow delivery structures to move thereon. Such tracks may also allow each delivery structure 40 to remain physically separated from each other. Body 20 may also include C-shaped troughs, posts, or other guiding mechanisms to allow each delivery structure 40 to remain physically separated from each other and to prevent each delivery structures 40 from forming a twisted configuration as each delivery structure is advanced or retracted through body 20.

Device 10 may also define any number or arrangement of ports 30. In embodiments where body 20 defines a plurality of ports 30 along the longitudinal axis thereof between distal end 410 and proximal end 400, and each of a plurality of delivery structures 40 are independently moveable through a respective one of the plurality of ports 30, body 20 may preferably also define at least one port 30, and more preferably a plurality of ports 30 at the distal end 410 of body 20 as illustrated in FIGS. 4D, 5, and 14. A plurality of delivery structures 40 are, in turn, extendable through the plurality of ports at distal end 410. Although not required to stay within the scope and spirit of the present invention, the plurality of delivery structures 40 extendable through the plurality of ports 30 at distal end 410 may be independently moveable with respect to each other of the plurality of delivery structures 40 extendable through the plurality of ports 30 at distal end 410 and/or each of the plurality of delivery structures 40 extendable through the plurality of ports along the longitudinal axis of body 20 between proximal end 400 and distal end 410.

Ports 30 may also be configured to allow each delivery structure 40 to exit body 20 at varying angles with respect to axis y of body 20. Preferably, the angle of exit is less than 90 degrees with respect to axis y. For example, referring to FIG. 4D, delivery structures 40 may exit ports 30 at an angle A in the range of about 10 to about 60 degrees with respect to axis y. The angle of exit of delivery structure 40 may be predetermined by providing a flexible guide near port 30 in body 20 to provide for the desired angle. Alternatively, delivery structures 40 themselves may be configured to exit body 20 at varying angles. For example, delivery structures 40 may be manufactured of a material that provides delivery structures 40 with a convex tensile bend or memory bend allowing angled exit through port 30 or allow delivery structures 40 to be preformed so that the distal ends curl out at a predetermined curvature when unconstrained by body 20. With respect to delivery structures 40 manufactured of a material to provide tensile bend, such material may include a string of silicone, resorbable biocomposite or any other suitable inert plastic polymer denser on either the concave or convex side of the bend. With respect to a material that provides delivery structures 40 with memory bend, such material may include shape memory alloy. Alternatively, body 20 may include tracks that are configured to operably engage delivery structures 40 and to guide delivery structures 40 to exit ports 30 along an angled trajectory. One skilled in the art would understand that other means may be used to provide for a desired exit angle and such means are encompassed by the present invention.

Figure 25:
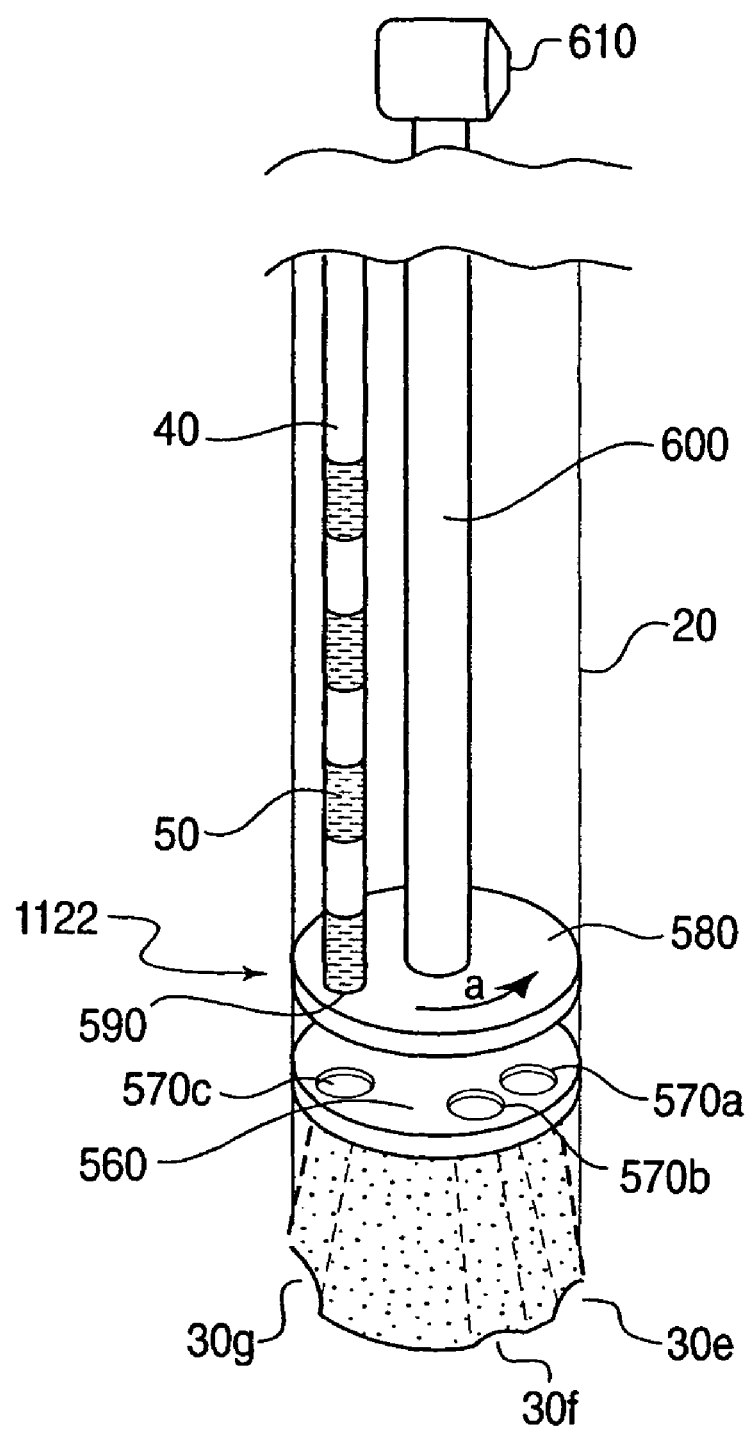
FIG. 25 is a partial interior view of an alternative embodiment of a device of the present invention.

The present invention also contemplates any number of delivery structures 40 independently moveable through a respective port 30 with any number of delivery elements 50 disposed thereon. Furthermore, delivery elements 50 can be arranged in any manner on delivery structures 40. For example, a delivery element 50 may be disposed on a distal section, medial section, and proximal section of delivery structure 40 (all such designs are in reference to embodiments of device 10 where delivery structures have delivery elements 50 disposed thereon). Although in preferred embodiment there are five delivery structures, and each delivery structure 40 is independently moveable through a single port 30, it is possible to have additional delivery structures 40 extend from any one port 30. Furthermore, body 20 may be designed such that a single delivery structure 40 can be capable of exiting two different ports 30. Such a configuration is particularly advantageous if a relatively fewer number, such as five or less, delivery structures 40 are desired to be employed. Referring to FIGS. 25 and 26, one embodiment that achieves this function includes a guide 560 located within body 20 and positioned proximal to ports 30. Guide 560 defines a plurality of angled through-holes 570a-c that angle from longitudinal axis y of body 20 toward ports 30. Therefore, through-holes 570a-c allow a delivery structure 40 to be advanced through a through-hole 570a-c and exit such throughhole along a predetermined trajectory determined by the angle of throughhole 570a-c. Device 10 further includes a disc 580 positioned proximal to guide 560 and that defines a single opening 590 through which a delivery structure 40 can pass and that is capable of rotating within body 20 about the longitudinal axis y of body 20 indicated by the arrow a. In this regard, a delivery structure 40 which passes through opening 590, can rotate about the longitudinal axis y and can be brought in registration above a selected throughhole 570 for deployment of the delivery structure 40 through the respective port 30e-g. Referring to FIG. 26, disc 580 allows a delivery structure 40 to be advanced through any of the througholes 570a-c and through any of the corresponding ports 30e-g. In one embodiment, to rotate disc 580, a stalk 600 connects the center of disc 580 to a rotary motor 610 positioned towards proximal end 400 of body 20. Stalk 600 would transfer rotational motion from rotary motor 610 to disc 580.

A neural stimulation delivery system including device 10 to stimulate neural tissue to affect a neurological condition may include other components useful in identifying, monitoring, or affecting a specific neural tissue site or a particular neurological condition associated with the specific neural tissue site. For example, such a system could include a component for lesioning and temperature monitoring, and/or a component that has a fiberoptic monitor which allows telemetric intracranial monitoring capabilities, and/or a microelectrode recording component, and/or a sensing component to incorporate a feedback mechanism to assist in determining whether the delivery structures should be adjusted. With respect to a sensing component, referring to FIG. 1, a sensor 550' can be incorporated with a system of stimulating neural tissue according to the present invention. Sensor 550' can be used with a closed-loop feedback system in order to automatically determine the level of stimulation necessary to provide the desired therapy. Sensor 550' may be implanted into a portion of a patient P's body suitable for detecting characteristics, symptoms or attributes of the condition or disorder being treated such as electrical brain activity, cerebral blood flow, and/or vital signs or other chemical and electrical activity of the body. Sensors suitable for use in a system according to the present invention include, for example, those disclosed in U.S. Pat. No. 5,711,316, which is incorporated by reference herein.

Furthermore, such a neural stimulation delivery system may also include a navigation system that provides the exact position/orientation of device 10 within the brain after delivery structures 40 are deployed. For example, if device 10 has a circular cross-section, the navigation system would provide the compass direction (i.e. degree) device 10 is positioned relative to a reference point in the brain, therefore assisting in the determination of which delivery structures 40 to deploy. Preferably the navigation system would incorporate some type of marker that is integral with device 10 or delivery structure 40 that would show up under computer tomography (CT) or magnetic resonance imaging (MRI) scanning techniques. According, the brain scans could be printed and fed into a computer having navigational software and a three-dimensional atlas of the patient's brain to model approximately where all the delivery structures 40 are positioned. The software may then be capable of providing instructions on where best to deploy delivery structures 40 or which delivery elements 50 to activate.

In use, delivery structures 40 of device 10 may be adjusted intra-operatively during an initial surgery when device 10 is implanted, during a minor surgery after device 10 is implanted in which only control mechanism 100 is accessed, or completely remotely in which case no surgery of any kind is required. With respect to intra-operative adjustment of delivery structures 40, a practitioner may initially place device 10 in the general region of a desired neural tissue site and then more precisely adjust the stimulation to the desired neural tissue site in situ by advancing or retracting a delivery structure 40 or specific combination of delivery structures 40. In such a circumstance, control mechanism 100 may rest atop the burr hole, within the burr hole, or above the burr hole under the scalp. With respect to adjusting delivery structures 40 after the initial surgery, a practitioner may initially place device 10 in the general region of a desired neural tissue site and then close the incision in the cranium. The practitioner may then more precisely adjust the stimulation to the desired neural tissue site on an out patient outpatient basis, by making a relatively small incision in the scalp to access the area control mechanism 100 is placed or to couple control mechanism 100 to the proximal ends 260 of delivery structures 40. The practitioner then adjusts the position of a delivery structure 40 or a specific combination of delivery structures 40. With respect to adjusting delivery structures 40 remotely, the practitioner may initially place device 10 in the general region of a desired neural tissue site and then close the incision in the cranium. The patient may then be transferred to a Neuromodulation Unit (NMU) where device 10 is non-invasively tested to achieve a desired effect. The position of delivery structures 40 may then be adjusted to a desired position to achieve a particular effect. This external adjustment of delivery structure 40 or a combination of delivery structures 40, allows the stimulation to be adjusted without having to perform a second surgery. The practitioner (or patient) may perform these adjustments of delivery structures 40 any time and as many times as necessary after device 10 is implanted as well. Such adjustments can be made under the visualization of computer tomography, magnetic resonance imaging, fluoroscopy, or the like and can be in response to a chemical, electrical, or any other physiological parameter including nerve action potentials, movement, blood flow, electroencephalograph signals, or normal vitals.

Although the invention has been described with reference to the preferred embodiments, it will be apparent to one skilled in the art that variations and modifications are contemplated within the spirit and scope of the invention. The drawings and description of the preferred embodiments are made by way of example rather than to limit the scope of the invention, and it is intended to cover within the spirit and scope of the invention all such changes and modifications.

We claim:

1. A stimulation delivery device for stimulating neural tissue comprising:
   a body having a proximal end and a distal end and defining a plurality of ports along the longitudinal axis thereof between the proximal end and the distal end of the body;
   a plurality of leads insertable within the body, each of the plurality of leads independently extendable through a respective one of the plurality of ports and;
   a control mechanism in communication with the plurality of leads to independently extend each of the plurality of leads through a respective one of the plurality of ports with respect to each other of the plurality of leads,
   wherein each of the plurality of leads has at least two electrodes thereon and each electrode is selectively powerable,
   wherein the control mechanism comprises a gear and clutch assembly.

2. The device of claim 1, further comprising at least one drug port.

3. The device of claim 1, further comprising a first delivery element disposed on the body, the first delivery element being either an electrode or drug port.

4. The device of claim 3, further including a second delivery element disposed on the body, the second delivery element being either an electrode or drug port.

5. The device of claim 4, wherein the first delivery element and the second delivery element are electrodes, the electrodes being selectively powerable.

6. The device of claim 1, wherein the plurality of leads is exitable through respective ones of the plurality of ports at an angle of less than 90 degrees with respect to the longitudinal axis of the body.

7. The device of claim 1, wherein the body further defines at least one additional distal port at the distal end thereof.

8. The device of claim 7, wherein at least one delivery structure is extendable through the at least one additional distal port.

9. The device of claim 1, wherein the plurality of leads is extendable between about 1 to about 10 millimeters from respective ones of the plurality of ports.

10. The device of claim 1, wherein the plurality of leads is capable of non-destructively stimulating neural tissue.

11. The device of claim 1, wherein the gear and clutch assembly is motorized.

12. The device of claim 1, further comprising a microelectrode recording device in communication with the stimulation delivery device.

13. The device of claim 1, further comprising at least one sensor in communication with the stimulation delivery device to detect a characteristic of the neurological condition being affecting.

14. The device of claim 1, further comprising a navigation system to detect the position of the stimulation delivery device within the brain.

15. The device of claim 1, wherein each of the plurality of leads has an electrode on the distal end of the lead and at least one additional electrode along the length thereof.

16. The device of claim 1, wherein the control mechanism is mechanical.

17. A stimulation delivery device for stimulating neural tissue comprising:
   a body having a proximal end and a distal end, the body defining an annular arrangement of a first plurality of ports between the proximal end and the distal end about a plane transverse to the longitudinal axis of the body;
   a first plurality of leads insertable in the body, each of the first plurality of leads independently extendable through a respective one of the first plurality of ports; and
   a control mechanism in communication with the plurality of leads to independently extend each of the plurality of leads through a respective one of the plurality of ports with respect to each other of the plurality of leads,
   wherein the control mechanism comprises a gear and clutch assembly.

18. The device of claim 17, wherein each of the first plurality of ports is situated 90 degrees apart from each other in the same annular plane.

19. The device of claim 17, wherein the body further defines an annular arrangement of a second plurality of ports between the first plurality of ports and the proximal end of the body about a plane transverse to the longitudinal axis of the body.

20. The device of claim 19, wherein each of the second plurality of ports is situated 90 degrees apart from each other in the same annular plane.

21. The device of claim 20, further comprising a second plurality of leads insertable in the body.

22. The device of claim 21, wherein the each of the second plurality of leads are independently extendable through a respective one of the second plurality of ports.

23. The device of claim 17, further comprising a first delivery element disposed on the body.

24. The device of claim 23, wherein the first delivery element extends approximately 360 degrees about the body.

25. The device of claim 23, wherein the first delivery element is an electrode divided into segments, each segment being selectively powerable.

26. The device of claim 17, wherein the body further defines at least one port at the distal end thereof.

27. The device of claim 26, wherein at least one delivery structure is extendable through the at least one port.

28. The device of claim 17, wherein the control mechanism is mechanical.

29. The device of claim 17, wherein each of the plurality of leads has at least two electrodes thereon and each electrode is selectively powerable.

* * * * *